United States Patent
Xiao et al.

(10) Patent No.: US 9,316,657 B2
(45) Date of Patent: Apr. 19, 2016

(54) APPARATUS AND METHOD FOR LOADING SAMPLES IN AN ANALYZER

(75) Inventors: Hua Xiao, Shenzhen (CN); Qisong Liu, Shenzhen (CN); Ping Tian, Shenzhen (CN); Kun Liu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 394 days.

(21) Appl. No.: 12/760,374

(22) Filed: Apr. 14, 2010

(65) Prior Publication Data

US 2010/0284777 A1 Nov. 11, 2010

(30) Foreign Application Priority Data

May 8, 2009 (CN) .......................... 2009 1 0107223

(51) Int. Cl.
*G01N 35/10* (2006.01)
*G01N 35/04* (2006.01)
*G01N 35/02* (2006.01)
G01N 35/00 (2006.01)

(52) U.S. Cl.
CPC .............. *G01N 35/04* (2013.01); *G01N 35/025* (2013.01); *G01N 2035/00287* (2013.01); *G01N 2035/00316* (2013.01); *G01N 2035/0465* (2013.01)

(58) Field of Classification Search
None
See application file for complete search history.

(56) References Cited

U.S. PATENT DOCUMENTS

| 4,933,147 | A |   | 6/1990 | Holler et al. |
|---|---|---|---|---|
| 5,510,082 | A | * | 4/1996 | Arai et al. ....................... 422/64 |
| 5,855,773 | A | * | 1/1999 | Lasota ......................... 210/146 |
| 2002/0025275 | A1 | * | 2/2002 | Oonuma et al. ................. 422/64 |
| 2002/0090729 | A1 | * | 7/2002 | Neeper et al. .................... 436/45 |
| 2004/0134239 | A1 | * | 7/2004 | Hapke et al. ................. 68/12.26 |
| 2007/0292941 | A1 | * | 12/2007 | Handique et al. .......... 435/288.7 |
| 2008/0220958 | A1 | * | 9/2008 | Hayasaka et al. ................. 494/7 |

FOREIGN PATENT DOCUMENTS

| CN | 1534298 A | 10/2004 |
|---|---|---|
| CN | 2862038 Y | 1/2007 |
| CN | 1942371 A | 4/2007 |
| CN | 101254486 A | 9/2008 |
| EP | 1653234 A1 | 5/2006 |
| EP | 1767949 A1 | 3/2007 |
| JP | 10-48195 * | 2/1998 |

(Continued)

OTHER PUBLICATIONS

International Search Report for Chinese Patent Application No. 200910107223.7.

(Continued)

*Primary Examiner* — P. Kathryn Wright
(74) *Attorney, Agent, or Firm* — Kory D. Christensen; Stoel Rives LLP

(57) ABSTRACT

What is disclosed are methods and apparatus for loading or removing samples for testing. The apparatus comprises a sample disk body for holding a sample for testing, a sample disk lid configured to cover at least a part of the sample disk body and comprising a fixed lid which is fixedly attached to the sample disk body and a movable gate which is movable relatively to the fixed lid, and a locking mechanism to lock the movable gate into a closed position. The opening and closing of the movable gate is controlled by the locking mechanism to prevent inadvertent opening of the sample lid while the sample disk is operating.

19 Claims, 5 Drawing Sheets

(56) References Cited

FOREIGN PATENT DOCUMENTS

| JP | 200717441 A | 1/2007 |
|---|---|---|
| WO | 2007097229 A1 | 8/2007 |

OTHER PUBLICATIONS

English Abstract of WO2007097229A.
English Abstract of JP200717441A.
English Abstract of CN1534298A.
English Abstract of CN1942371A.
English Abstract of CN101254486A.
English Abstract of CN2862038Y.
English Abstract of EP1653234A.
English Abstract of EP 1767949A.
Testing Serum Uricacid Using an Auto Biochemical Analyzer.
English Abstract of "Testing Serum Uricacid Using an Auto Biochemical Analyzer".

\* cited by examiner

APPARATUS AND METHOD FOR LOADING SAMPLES IN AN ANALYZER

CROSS-REFERENCE TO RELATED APPLICATIONS

This application claims priority to Chinese Patent Application No. 200910107223.7, filed on May 8, 2009, which is hereby incorporated by reference in its entirety.

TECHNICAL FIELD

Various embodiments are directed at a method and a device for loading samples for a biochemical analyzer.

BACKGROUND ART

For conventional biochemical analyzers, a protective cover of the analyzer needs to be opened or even removed so to remove the lid for the sample disk when loading a sample. After the sample is loaded, the sample disk lid and the protective cover are returned to their respective original positions. In this conventional biochemical analyzer, operations may be tedious. In addition, after the lid for the sample disk has been opened or removed, the sample disk may still be rotating or may start to rotate. In this case, loading and unloading the sample may pose some potentially dangerous conditions.

SUMMARY

An object of various embodiments is to provide a sample loading device for biochemical analyzers and a method for loading samples into a biochemical analyzer or other devices.

Various embodiments comprise a sample loading device for biochemical analyzers, the sample loading device comprising: a sample disk body which is configured to load a sample to be used for further testing; a sample disk lid which is configured to completely or partially cover the sample disk body, wherein the sample disk lid comprises a fixed lid that is fixedly attached to the sample disk body and a movable gate that is movable with respect to the fixed lid; and a locking mechanism that is configured to exhibit a locked state in which the movable gate is locked in a closed position. In various embodiments, the fixed lid is fixedly attached to the sample disk body yet may still be removed from the sample loading device. For example, the fixed lid may be fixedly attached to the sample disk body by using, for example, one or more fasteners or other similar devices so the fixed lid may be removed by, in the case where one or more fasteners are used to attach the fixed lid, undoing the one or more fasteners.

In one embodiment, the locking mechanism comprises a controller and a controlled, electrical, mechanical, or electromechanical lock where the controller is configured to control the controlled, electrical, mechanical, pneumatic, or electromechanical lock to close and open the movable gate.

In the single embodiment or in some embodiments, the sample loading device may further optionally comprise one or more sensors that are arranged, for example, on the sample disk body for detecting whether the movable gate is in a closed or open position. The one or more sensors may also be located in other position(s) or part(s) of the device to serve substantially the same purpose for detecting the position of the movable gate.

In the single embodiment or in some embodiments, the one or more sensors comprise a magnetic sensor which interacts with a magnet that may be positioned, for example, on the movable gate. In this embodiment, the magnetic sensor measures or detects the magnetic field of the magnet and converts the magnetic field into a signal which may be read to indicate the position of the movable gate. In the same embodiment or in other embodiments, the one or more sensors may comprise other types of sensors such as linear encoders, optical/light sensors, electro-optical sensors, any suitable types of position sensors, or a combination of any of the above. Some exemplary position sensors comprise an inductive non-contact position sensor, a piezo-electric transducer, a proximity sensor based on electromagnetic or electrostatic field or some form of electromagnetic radiation, or an electronic proximity sensor. One of ordinary skill in the art will clearly understand that the above types of sensors do not intend to be limiting, and that other types of sensors that serves same or similar purposes also fall within the scope of various embodiments.

In the single embodiment or in some embodiments, the locking mechanism further comprises a manual unlocking mechanism or device.

Some embodiments are directed at a biochemical analyzer comprising a sample loading device that is described in some embodiments as exemplified above.

Some embodiments are directed at a sample loading method for biochemical analyzers—The method comprises the act of, locking the movable gate by using a locking mechanism as described above after a sample to be tested has been loaded into a sample disk, and a movable gate has been closed. The method may further comprise unlocking the movable gate by manipulating or undoing, for example, the locking mechanism when the sample needs to be replaced.

In the single embodiment or in some embodiments, the locking mechanism automatically locks the movable gate by means of an elastic device such as a spring.

In the single embodiment or in some embodiments, the locking mechanism comprises a controller and controlled, mechanical, electrical, or electromechanical lock where the controller may be configured to control the controlled, mechanical, electrical, or electromechanical lock to lock and unlock the movable gate.

Some embodiments are directed at a sample loading device for biochemical analyzers. The sample loading device comprises a sample disk body and a sample disk lid, wherein the sample disk body may be configured to load a sample to be used for testing, the sample disk lid may be configured to completely or partially cover the sample disk body; and a locking mechanism which may be configured to exhibit one or both of the locked state and the unlocked state. In some embodiments when the locking mechanism is in the locked state, the locking mechanism locks the sample disk lid in a position for completely or partially covering the sample disk body so that the sample disk lid is unmovable. In some embodiments where the locking mechanism is in the unlocked state, the sample disk lid is movable with respect to the sample disk body.

In the single embodiment or in some embodiments, the movable gate is movable with respect to the fixed lid and may be locked to a closed position by means of the locking mechanism to ensure that the sample(s) may not be removed from or added into the sample loading device while the sample disk is rotating or spinning to improve safety.

DETAILED DESCRIPTION

The features and advantages of the invention will be described in details by way of one or more illustrative embodiments with reference to the drawings.

Figure 1:
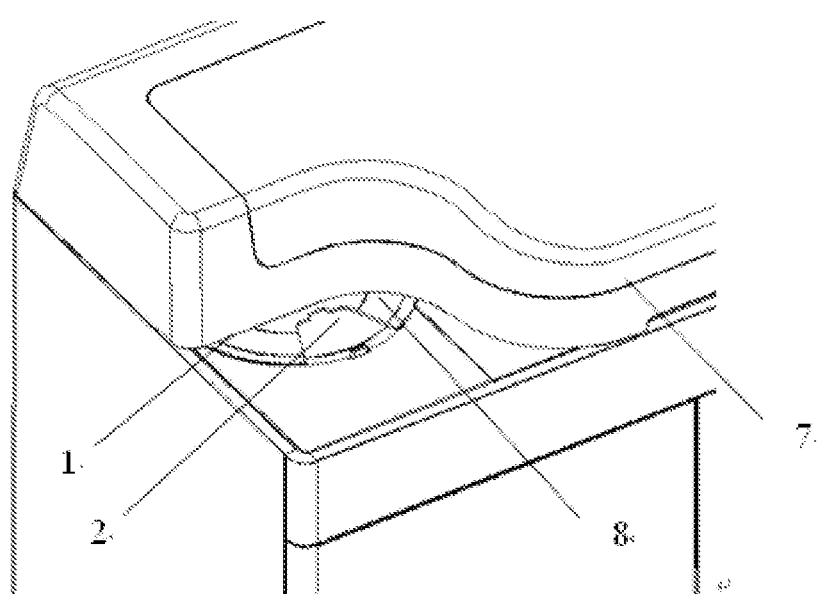
FIG. 1 illustrates a partial view of a biochemical analyzer having a sample loading device according to an embodiment of the invention.
Figure 2:
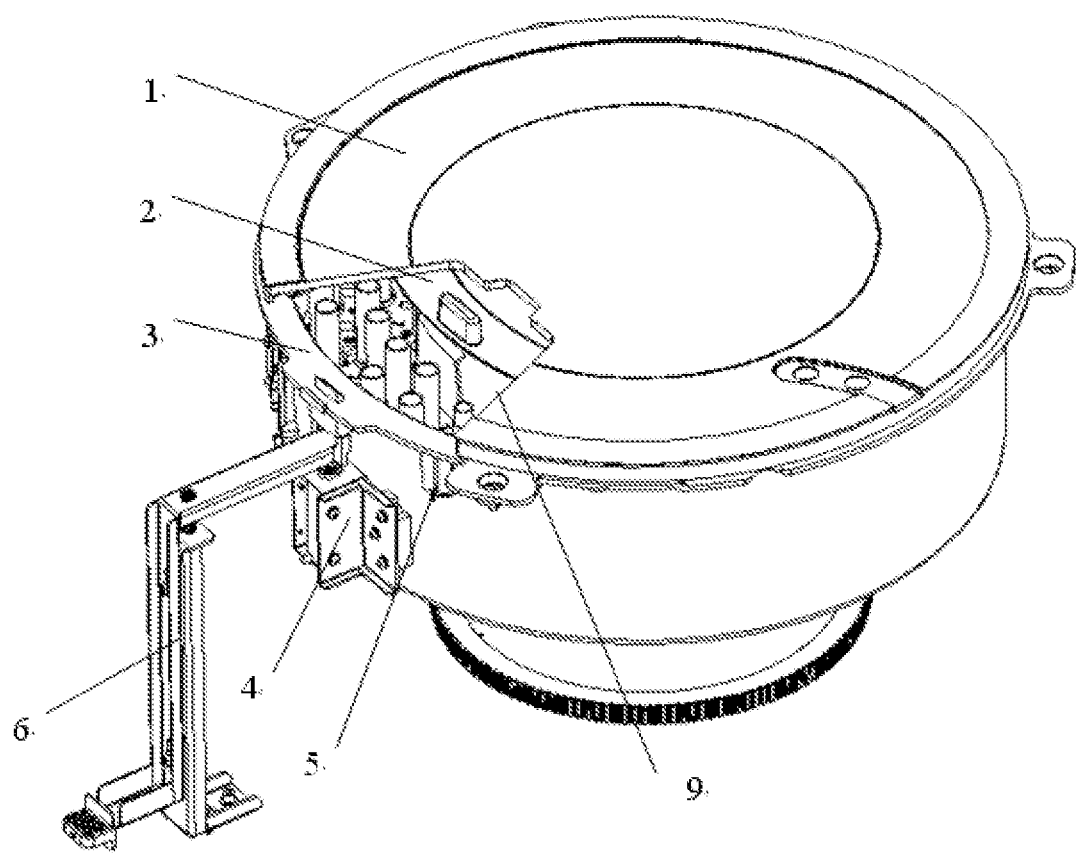
FIG. 2 illustrates a structural view of the sample loading device according to the embodiment of the invention.
Figure 3:
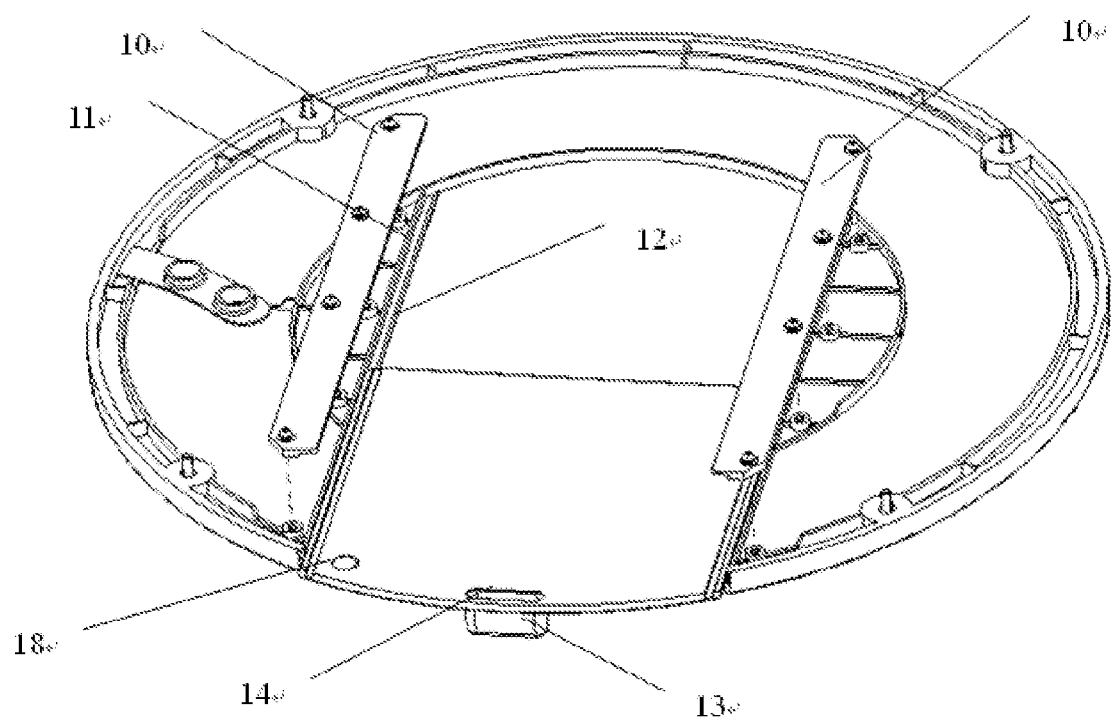
FIG. 3 illustrates a schematic view of the back side of the sample loading device according to the embodiment of the invention.
Figure 4:
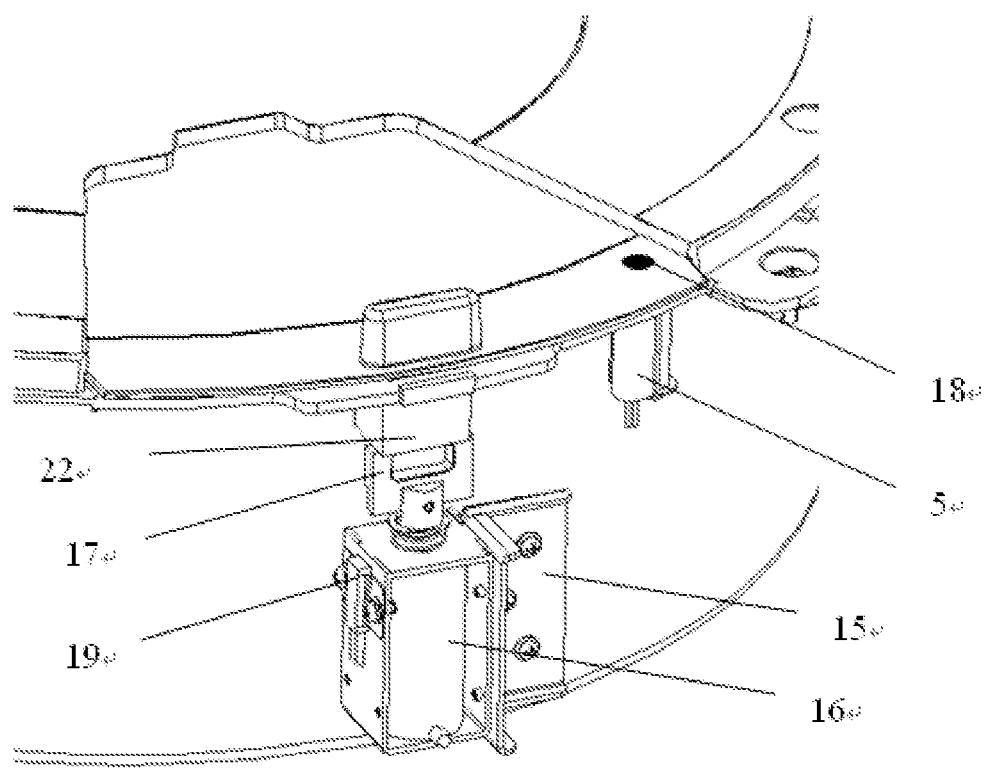
FIG. 4 illustrates a schematic view showing the structure of an electromagnetic lock according to an embodiment of the invention.
Figure 5:
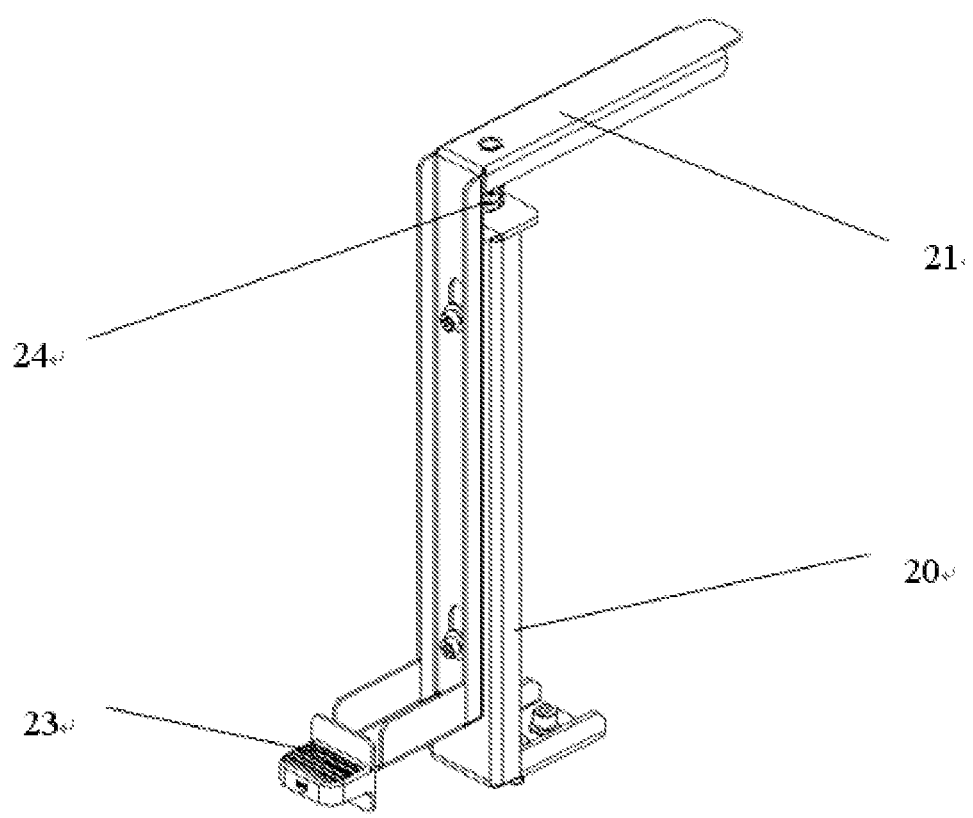
FIG. 5 illustrates a schematic view showing the structure of a manual unlocking device according to an embodiment of the invention.

Referring to FIG. 1 which illustrates biochemical analyzer comprising a sample loading device. In some embodiments, the sample loading device comprises a sample disk lid 1, a sample disk body 3, and a locking mechanism. In these embodiments as illustrated in FIG. 1, the biochemical analyzer comprises a mechanical locking mechanism. Nonetheless, other types of locking mechanism may also be used to achieve similar purposes. The locking mechanism in the illustrative example comprises a mechanical lock. In other embodiments, the locking mechanism may also comprise an electrical or an electromechanical lock. After a sample to be tested is placed in the sample disk, the locking mechanism locks the sample disk lid 1 onto sample disk body 3 so that the sample disk lid 1 may not be opened unless and until the locking mechanism is deactivated in some embodiments. In the case where the sample needs to be replaced or removed, the lock may be deactivated or released to allow the sample disk lid to be opened and/or to put in a new sample to be tested.

In the same embodiments or in other embodiments, the sample loading device comprises a sample disk lid 1, a sample disk body 3 and a locking mechanism. The sample disk lid 1 comprises a fixed lid 8, which is fixedly attached to the sample disk body, and a movable gate 2, which is movable relative to the fixed lid in some embodiments. The locking mechanism comprises an electrical or an electromagnetic lock 4 and a controller which controls the locking and unlocking of the electrical or electromagnetic lock 4 in these embodiments or in other embodiments. As shown in FIG. 1, the sample loading device for biochemical analyzer may further comprise a magnetic sensor 5 and an unlocking device 6 in some embodiments. In some embodiments, the unlocking device may comprise a manual unlocking device. In these embodiments or in some embodiments, at least a portion of the sample disk lid 1 is covered by a protective cover 7, and the remaining portion of the sample disk lid is not covered the protective cover 7. The exposed portion of the sample disk lid 1 comprises a cutout section 9, and the movable gate 2 may be mounted in a way that the movable gate 2 may be used to close or open the cutout section 9. For example, in some embodiments, the movable gate 2 may be movably attached, for example underneath or atop the sample disk lid or other parts of the sample loading device such that one may slide the movable gate 2 in a radial direction or in an angular direction to open and to close the cutout section 9. In these embodiments, the sample loading device allows to load the sample after the movable gate 2 has been slid open, without the need of opening the protective cover 7 of the device and the sample disk lid 1.

In these embodiments, the electromagnetic lock 4, which may be mounted to, for example, the sample disk body 3, locks the movable gate 2 after the movable gate 2 is moved to a closed position. Further, the magnetic sensor 5, which may also be mounted to, for example, the sample disk body 3, detects the open or closed state of the movable gate 2 by sensing the position of a magnet assembly which may be mounted to the movable gate 2 in some embodiments, and feeds back the detection result of the position to the controller of the biochemical analyzer for controlling the rotation or spinning and for stopping the sample disk. In these embodiments, when the magnetic sensor 5 detects that the movable gate 2 is in the open position, the controller causes the sample disk to stop rotating or spinning. In these embodiments, the sample disk is allowed to rotate when the movable gate 2 is in the closed position. In some embodiments where it is determined that the movable gate 2 needs to be opened to perform, for example, sample loading or removal, the sample loading device causes the rotation of the sample disk to stop and the electromagnetic lock to be released. In these embodiments, any potential danger of loading or removing the sample while the sample disk is still rotating or spinning may be effectively reduced or completely avoided.

Further details of the second embodiment will be described now. In these embodiments or in other embodiments, the exposed portion of the sample disk lid 1 comprises the cutout 9 as described above and two strips 10 which may be mounted, for example, to the back side of the sample disk lid 1. The back side of the sample disk lid 1 may further comprise two restricting ribs. For example, the sample disk lid 1 may comprises one or more ribs 11, which extend along the sliding direction of the movable gate 2 and restrain the movable gate 2 from exhibiting lateral movement relative to the one or more ribs 11. Other means for restraining the lateral movement of the movable gate 2 may also be used to achieve similar purposes. The sample disk lid 1 may also comprise two or more ribs 12 which function jointly with the one or more strips 10 for restraining the movable gate 2 from moving in the vertical direction which indicates the direction perpendicular to the surface of the one or more strips 10. In these embodiments, the one or more ribs 11 may be configured to vertical motion, and the moveable gate 2 may be configured to limit the lateral movement of the moveable gate 2. The sample disk lid 1 may also comprise two guiding slots or rails for guiding the movement of the movable gate 2 to the open and closed positions. In the case where the movable gate 2 is in the open position, sample loading or removal may be performed through the cutout 9, in the case where the movable gate 2 is in the closed position, the movable gate 2 at least partially covers the cutout 9 so as to prevent sample loading or removal. In these embodiments, the movable gate 2 slides open and close along the guiding slots or rails in the radial direction. One of ordinary skill in the art will certainly appreciate the fact that the movable gate 2 may also be configured to flip open and close relatively to the sample disk lid 1 or to rotates open and close along an angular direction to achieve the same or similar purpose. For example, the movable gate 2 may be designed and configured in a way that flips open to allow or to prevent access to the samples for sample removal or sample addition in some embodiments. The movable gate 2 may also be designed or configured in a way to open and close in an angular direction similar to the shutter action of a camera system to open and close the cutout 9 to allow or to prevent access to the samples for sample removal or sample addition in some embodiments.

In some embodiments, the sample disk lid 1 or the movable gate 2 may comprise a portion above the samples that is made of a transparent or translucent material to allow an operator or a detection device to see through such a transparent or translucent material. The movable gate 2 may optionally comprise a handle 12 that may be manipulated by an operator. The moveable gate 2 may further optionally comprise a gate latch slot 13, which accommodates a latch for the movable gate 2 and corresponds to the electromagnetic lock. The locking of the movable gate 2 may be achieved by the electromagnetic lock 4. The electromagnetic lock 4 may be mounted to the sample disk body 3 by, for example, one or more fasteners via an electromagnet mount 14 in some embodiments. The sample loading device may further optionally comprise a gate latch 16 which moves up and down according to the electromagnetic force from an electromagnet 15. When the gate latch 16 is positioned in the gate latch slot 13 of the movable gate 2, the movable gate 2 is locked. When the gate latch 16 moves out of the gate latch slot 13, the movable gate 2 becomes unlocked in these embodiments. The open and closed states of the movable gate 2 may be sensed by the magnetic sensor 5, which may be mounted to, for example, the sample disk body 3. The triggering end of the magnetic sensor 5 comprises a magnet assembly 17 that is mounted at a position opposite to the movable gate 2 to detect whether the movable gate 2 is in an open or a closed position in some embodiments.

In order to prevent the electromagnet 15 from reaching an abnormal temperature state, which may present another potentially dangerous condition, the sample loading device may also optionally comprise a temperature protective switch or a thermal switch 18 that may be mounted to, for example, the electromagnet 15 in some embodiments. In these embodiments, the thermal switch or the temperature protective switch 18 may be set at to trigger a signal if it senses that the temperature of the electromagnet 15 reaches a predetermined threshold temperature. For example, the switch 18 may transmit a signal to shut off power to the electromagnet 15 if the switch 18 senses that the temperature electromagnet 15 is close to a maximum allowable touch temperature of 65 degrees Celsius. In some embodiments, the front end of the movable gate 2 or the gate latch 16 may comprise one or more features so that when the movable gate 2 is backing the closed position, the one or more features activate the gate latch 16. For example, such one or more features may comprise, for example, a chamfered or a rounded surface which, when in contact with the gate latch 16, activates the gate latch 16 and causes the gate latch 16 to move into the gate latch slot 13 to lock the movable gate 2 in some embodiments. When the biochemical analyzer is powered off, the movable gate 2 is in a locked state in some embodiments. In some embodiments, the movable gate 2 may be opened by means of the manual unlocking device 6 or another similar type of manual override. The manual unlocking device comprises a mount 19, a strip 20, a handle 23, and a spring 24 in some embodiments. The strip 20 comprises an end that is inserted into a slot 22 of the gate latch 2, and another end that is attached to the handle 23. In these embodiments, pushing down the handle 23 moves the strip 20 downwardly under the guidance of the mount 19, which causes the gate latch 16 to move downwardly away from the gate latch slot 13, and thus unlock the movable gate 2 in some embodiments. When the handle 23 is moved, the return spring 24 may be designed or configured to become compressed and stores elastic energy. When the handle 23 is released, the elastic energy stored in the spring 24 causes the strip 20 to return back to its original position.

Some embodiments are further directed at a method for loading samples in a normal state.

In some embodiments, the method for loading samples comprises unlocking the electromagnetic lock 4 by energizing the electromagnetic lock 4. The method may further comprise disengaging the locking mechanism to allow the movable gate 2 to open. For example, the method may cause the gate latch 16 to move out of the gate latch slot 13 by using the magnetic force from the electromagnet 15 in some embodiments.

The method for loading sample may further comprise detecting whether the movable gate 2 is in an open or a closed position in some embodiments. The method may also comprise preventing the sample disk from spinning or rotating by deactivating the electromagnetic lock 4 by using the magnetic sensor 5, where it is determined that the movable gate 2 is in an open position. For example, the method may, after it is determined that the movable gate 2 is in an open position, may use the magnetic sensor 5 to command the electromagnetic lock 4 to be de-energized so that the gate latch 16 extends out to prevent the sample disk from rotating or spinning in some embodiments.

After the operator finishes sample loading or removal, the method may further comprise locking the movable gate 2 by, for example, pulling back the movable gate 2 to engage the gate latch 15 with the gate latch slot 13 in some embodiments. In these embodiments, the method further comprises determining whether the movable gate 2 is in a closed position by using the magnetic sensor 5 and sending a signal to the analyzer to indicate the position of the movable gate. In the case where it is determined that the movable gate 2 is in a closed position, the method allows the sample disk to operate as intended.

In the case where the biochemical analyzer is powered off, the method allows an operator to perform sample loading or removal operation in some embodiments as described below.

In these embodiments, the method comprises opening the front gate of the analyzer to expose the handle 23 of the manual unlocking device 6. The method further comprises unlocking the movable gate 2 by manipulating the handle 23. For example, in the illustrative examples as shown in FIGS. 1-4, the method comprises pushing down the handle 23 to unlock the movable gate 2. The method further comprises opening the movable gate 2 after the movable gate 2 is unlocked. In addition, the method comprises loading or removing samples after the movable gate 2 becomes opened.

After the sample loading or removal is completed, the method comprises closing the movable gate 2 and locking the movable gate 2.

Some embodiments are directed at a sample loading device for biochemical analyzers. The sample loading device comprises a sample disk body and a sample disk lid that is configured to at least partially cover the sample disk body. The sample disk lid comprises a fixed lid and a movable gate which may be opened to provide access to the samples.

The sample loading device further comprises a locking mechanism which locks the movable gate when the movable gate is in the closed position in some embodiments.

The above figures and description provide illustrative examples of certain ways to implement some embodiments of the methods or systems. Those skilled in the art may also design the cutout of the sample disk lid and the movable gate in other shapes, such as polygonal shapes, circular shapes, irregular shapes, etc. For example, the movable gate may be designed to comprise a circular section, and the back side of the sample disk lid may comprise two arc-shaped strips so that the movable gate be operated in a circumferential or angular direction in place of sliding in a linear direction. In another modification, a sensor of other types may be used for detecting the open and closed positions of the movable gate. For example, a photoelectric sensor may be mounted to a sample pot, and a sensing plate may be mounted to the movable gate. The opening and closing of the movable gate may alternatively be controlled by means of an automatic device, such as a motor, a hydraulic or pneumatic transmission mechanism, or the like so that the opening and closing operation of the movable gate may be performed automatically in place of manual operation. Alternatively, the sample disk lid may not cover the sample disk body. Instead, the sample disk lid covers a table of the biochemical analyzer which corresponds to the sample disk body. The locking mechanism may comprise a conventional mechanical lock or an electrically controlled lock, or other locking devices. The locking mechanism may be attached to the sample disk body, to the sample disk lid, or to other parts of the biochemical analyzer. The method for loading or removing samples may incorporate automatic locking or manual or electrical locking. The unlocking process may be performed manually or via electrical unlocking.

Furthermore, a reagent disk may comprise a loading device similar to the sample loading device disclosed herein.

Various embodiments described herein are not intended to limit the scope of the claims in this Application or in related applications. One of ordinary skill in the art will readily recognize that modifications and changes may be made to the embodiments described herein without departing from the spirit of various embodiments of the invention. Accordingly all these modifications and changes may be regarded as falling within the scope of various embodiments of the invention.

We claim:

1. A sample or a reagent loading device for a biochemical analyzer, comprising:
   a disk body that is to load a sample or one or more reagents to be used for one or more tests;
   a disk lid that is to cover at least a part of the disk body, the disk lid comprising a fixed lid, which is fixedly attached to the disk body, a movable gate which is movable relative to the fixed lid, and guiding slots or rails upon which the movable gate slides along the disk lid to an open position or a closed position;
   a protective cover that is to cover a portion of the disk lid but not a remaining portion of the disk lid to expose at least a part of the movable gate for loading or unloading the sample or the one or more reagents, wherein the loading or unloading the sample or the one or more reagents does not require removing or opening the protective cover;
   a locking mechanism that comprises a lock attached to the disk body that extends upward to engage the movable gate, the locking mechanism including a locking state in which the movable gate is locked into the closed position;
   a sensor that is to detect a position of the movable gate and is to send detection result of the position of the movable gate to a controller that is to cause start and stop of motion of a disk for the sample or the one or more reagents and to prevent the disk from spinning or rotating based at least in part on the position of the movable gate,
   wherein the locking mechanism further comprises an electromagnet, for locking and unlocking the movable gate, the loading device also comprise a temperature protective switch or a thermal switch, if the temperature of the electromagnet reaches a predetermined threshold value, the switch transmits a signal to shut off power to the electromagnet.

2. The sample or the reagent loading device of claim 1, wherein the locking mechanism comprises the controller and the lock, the controller being configured to control the lock to lock and unlock the movable gate.

3. The sample or the reagent loading device of claim 1, wherein the sensor comprises a magnetic sensor, and the movable gate comprises a magnet that interacts with the magnetic sensor.

4. The sample or the reagent loading device of claim 1, wherein the locking mechanism includes a manual unlocking mechanism that comprises a mount, strip and handle, the manual unlocking mechanism configured to unlock the movable gate when the handle is moved which causes the strip to move under the guidance of the mount which releases a lock engagement with the movable gate.

5. The sample or the reagent loading device of claim 4, wherein the manual unlocking mechanism is configured such that when the biochemical analyzer is powered off and the movable gate is in a lock state, the movable gate is openable by the manual unlocking mechanism.

6. The sample or the reagent loading device of claim 1, wherein:
   the sensor comprises a sensing feature, which is attached to the movable plate, and a photoelectric sensor, and
   the sensor is to control locking and unlocking actions of the locking mechanism.

7. The sample or the reagent loading device of claim 1, wherein the disk lid comprises at least one restricting rib and at least one strip functioning in combination to restrain the movable gate from moving in a vertical direction.

8. A biochemical analyzer for analyzing one or more samples, comprising:
   a disk body that is to load a sample or a reagent to be used for one or more tests;
   a disk lid that is to cover at least a part of the disk body, the disk lid comprising a fixed lid, which is fixedly attached to the disk body, a movable gate which is movable relative to the fixed lid; and guiding slots or rails upon which the movable gate slides along the disk lid to an open position or a closed position; and
   a protective cover that is to cover a portion of the disk lid but not a remaining portion of the disk lid to expose at least a part of the movable gate for loading or unloading the sample or the reagent, wherein the loading or unloading the sample or the reagent does not require removing or opening the protective cover;
   a locking mechanism that comprises a lock attached to the disk body that extends upward to engage the movable gate, the locking mechanism including a locking state in which the movable gate is locked into the closed position;
   a sensor that is to detect a position of the movable gate and to send detection result of the position of the movable gate to a controller that is to cause start and stop of motion of a disk for the sample or the reagent and to prevent the disk from spinning or rotating based at least in part on the position of the movable gate; and
   an analysis module that is to analyze the sample,
   wherein the locking mechanism further comprises an electromagnet, for locking and unlocking the movable gate, the biochemical analyzer also comprises a temperature protective switch or a thermal switch, if the temperature of the electromagnet reaches a predetermined threshold value, the switch transmits a signal to shut off power to the electromagnet.

9. The biochemical analyzer of claim 8, wherein the locking mechanism comprises the controller and the lock, in which the controller is to control the lock to lock and unlock the movable gate.

10. The biochemical analyzer of claim 8, wherein the sensor comprises a magnetic sensor, and the movable gate comprises a magnet that interacts with the magnetic sensor.

11. The biochemical analyzer of claim 8, wherein the locking mechanism comprises a manual unlocking mechanism.

12. A method for handling a sample or a reagent in a biochemical analyzer, comprising:
  powering on the biochemical analyzer, wherein
    the biochemical analyzer comprises a disk lid that comprises a first lid, which is fixedly attached to the biochemical analyzer, a movable gate, which moves relatively to the first lid, and guiding slots or rails upon which the movable gate slides along the disk lid to an open or a closed position,
  covering a portion but not a remaining portion of the disk lid with a protective cover to expose at least a part of the movable gate for loading or unloading a sample or a reagent, wherein the loading or unloading the sample or the reagent does not require removing or opening the protective cover;
  using a sensor to detect a position of the movable gate and to send detection result of the position of the movable gate to a controller that is to cause start and stop of motion of a disk and to prevent the disk from spinning or rotating based at least in part upon the position of the movable gate; and
  closing the movable gate, wherein the act of closing the movable gate automatically engages a locking mechanism to lock the movable gate, the locking mechanism extending upward to engage with the movable gate,
  wherein the locking mechanism further comprises an electromagnet, for locking and unlocking the movable gate, the biochemical analyzer also comprise a temperature protective switch or a thermal switch, if the temperature of the electromagnet reaches a predetermined threshold value, the switch transmits a signal to shut off power to the electromagnet.

13. The method of claim 12, wherein the locking mechanism automatically locks the movable gate by using a return spring.

14. The method of claim 12, wherein the locking mechanism comprises the controller and a lock, and the controller is to control the lock to lock or unlock the movable gate.

15. The method of claim 12, wherein the act of loading or unloading the sample or a reagent is performed without removing the first lid.

16. The method of claim 12, further comprising opening preventing the disk assembly from operating based at least in part upon the position of the movable gate, wherein the sensor detects that the position of the movable gate is not at a closed position.

17. A sample or a reagent loading device for an analyzer, comprising:
  a disk body and a disk lid, wherein
    the disk body is to load a sample or a reagent to be tested, and the disk lid is to cover at least a part of the disk body and comprises a movable gate and guiding slots or rails upon which the movable gate slides along the disk lid to an open position or a closed position;
  a protective cover that is to cover a portion but not a remaining portion of the disk lid to expose at least a part of the movable gate for loading or unloading a sample or a reagent for testing, wherein the loading or unloading the sample or the reagent does not require removing or opening the protective cover;
  a locking mechanism comprising a lock attached to the disk that extends upward to engage the movable gate, the locking mechanism configured to have at least a locking state and an unlocking state, wherein
    in the locking state, the locking mechanism locks the sample disk lid in a position for covering the at least a part of the disk body so that the disk lid is unmovable; and
  a sensor that is to detect a position of the movable gate and is to send detection result of the position of the movable gate to a controller that is to cause start and stop of motion of a disk for the sample or the one or more reagents and to prevent the disk from spinning or rotating based at least in part on the position of the movable gate,
  wherein the locking mechanism further comprises an electromagnet, for locking and unlocking the movable gate, the loading device also comprise a temperature protective switch or a thermal switch, if the temperature of the electromagnet reaches a predetermined threshold value, the switch transmits a signal to shut off power to the electromagnet.

18. The sample or reagent loading device of claim 17, wherein:
  the disk is to rotate or spin when the sensor detects that the movable gate is at a closed position, and
  the sensor is to cause the locking mechanism to lock the movable gate when the sensor detects that the movable gate is at the closed position.

19. The sample or reagent loading device of claim 17, wherein:
  the sensor is to issue a signal to stop or prevent the disk from rotating or spinning when the sensor detects that the movable gate is at an open position, and
  the sensor is to cause the locking mechanism to unlock the movable gate when the sensor detects that the movable gate is at the open position.

* * * * *